United States Patent [19]
Steiner et al.

[11] Patent Number: 6,071,497
[45] Date of Patent: Jun. 6, 2000

[54] MICROPARTICLES FOR LUNG DELIVERY COMPRISING DIKETOPIPERAZINE

[75] Inventors: Solomon S. Steiner, Mt. Kisco; Robert Feldstein, Dobbs Ferry; Huiling Lian, Yonkers, all of N.Y.; Christopher A. Rhodes, Stamford, Conn.; Gregory S. Shen, Hartsdale, N.Y.

[73] Assignee: Pharmaceutical Discovery Corporation, Elmsford, N.Y.

[21] Appl. No.: 08/847,352

[22] Filed: Apr. 24, 1997

Related U.S. Application Data

[63] Continuation of application No. 08/441,378, May 15, 1995.
[51] Int. Cl.[7] ......................................................... A61K 9/12
[52] U.S. Cl. ................................ 424/45; 424/46; 424/489
[58] Field of Search ................................. 424/45, 46, 489

[56] References Cited

U.S. PATENT DOCUMENTS

| | | |
|---|---|---|
| 4,272,398 | 6/1981 | Jaffe . |
| 4,861,627 | 8/1989 | Mathiowitz . |
| 5,145,684 | 9/1992 | Liversidge et al. . |
| 5,260,306 | 11/1993 | Boardman et al. . |
| 5,352,461 | 10/1994 | Feldstein et al. . |
| 5,653,961 | 8/1997 | McNally et al. . |

FOREIGN PATENT DOCUMENTS

| | | |
|---|---|---|
| 0 257 915 | 3/1988 | European Pat. Off. . |
| 91/04011 | 4/1991 | WIPO . |
| 93/18754 | 9/1993 | WIPO . |

OTHER PUBLICATIONS

Benita, et al., "Characterization of Drug–Loaded Poly(d, l–lactide) Microspheres," *J. Pharm. Sci.*, 73, 1721–1724 (1984).

Gupta, et al., "Contemporary Approaches in Aerosolized Drug Delivery to the Lung," *J. Controlled Release*, 17(2), 127–147 (1991).

Katchalski, et al., "Synthesis of Lysine Anhydride," *J. Amer. Chem. Soc.*, 68, 879–880 (1946).

Kopple, et al., "A Convenient Synthesis of 2,5–Piperazinediones," *J. Org. Chem.*, 33(2), 862–864 (1968).

Lim, et al., "Microencapsulation of Living Cells and Tissues," *J. Pharm. Sci.*, 70, 351–354 (1981).

Mathiowitz, et al., "Polyanhydride Mocrospheres as Drug Carriers. II. Microencapsulation by Solvent Removal," *J. Appl. Polymer Sci.*, 35, 755–774 (1988).

Mathiowitz, et al., "Novel Microcapsules for Delivery Systems," *Reactive Polymers*, 6, 275–283 (1987).

Mathiowitz, et al., "Polyanydride Microspheres. IV. Morphology and Characterization of Systems Made by Spray Drying," *J. Appl. Polymer Sci.*, 45, 125–134 (1992).

Mathiowitz, et al., "Morphology of Polyanyhdride Microsphere Delivery Systems," *Scanning Microscopy*, 4, 329–340 (1990).

Mathiowitz and Langer, "Polyanhydride Microspheres As Drug Carrier. I. Hot–Melt Microencapsulation," *J. Controlled Release*, 5, 13–22 (1987).

Salib, et al., "Utilization of Sodium Alginate in Drug Microencapsulation," *Pharazeutische Industrie*, 40: Nr. 11a, 1230–1234 (1978).

Sawhney, et al., "Bioerodible Hydrogels Based on Photopolymerized Poly(ethylene glycol)–co–poly(a–hydroxy acid) Diacrylate Macromers," *Macromolecules*, 26: 581–587 (1993).

Witchert, et al., "Low Molecular Weight PLA: A Suitable Polymer for Pulmonary Administered Microparticles," *J. Microencapsulation*, 10(2), 195–207 (1993).

*Primary Examiner*—Raj Bawa
*Attorney, Agent, or Firm*—Arnall Golden & Gregory, LLP

[57] ABSTRACT

Drug delivery to the pulmonary system has been achieved by encapsulation of the drug to be delivered in microparticles having a size range between 0.5 and ten microns, preferably in the range of two to five microns, formed of a material releasing drug at a pH of greater than 6.4. In a preferred embodiment, the drug delivery system is based on the formation of diketopiperazine microparticles which are stable at a pH of 6.4 or less and unstable at pH of greater than 6.4, or which are stable at both acidic and basic pH, but which are unstable at pH between about 6.4 and 8. Other types of materials can also be used, including biodegradable natural and synthetic polymers, such as proteins, polymers of mixed amino acids (proteinoids), alginate, and poly (hydroxy acids). In another embodiment, the microparticles have been modified to effect targeting to specific cell types and to effect release only after reaching the targeted cells.

14 Claims, 2 Drawing Sheets

MICROPARTICLES FOR LUNG DELIVERY COMPRISING DIKETOPIPERAZINE

This application is a continuation of U.S. Ser. No. 08/441,378, filed May 15, 1995.

BACKGROUND OF THE INVENTION

This invention is generally in the area of drug delivery systems and is particularly related to methods of delivery to the lungs and other components of the pulmonary system.

Many drugs are delivered to the lungs where they are designed to have an effect on the tissue of the lungs, for example, vasodilators or surfactants, or within the bronchi, for example, a bronchodilator, or on a tissue within the lung, for example, a chemotherapeutic agent. Other drugs, especially nucleotide drugs, have been delivered to the lungs because it represents a tissue particularly appropriate for treatment, for example, for genetic therapy in cystic fibrosis, where retroviral vectors expressing a defective adenosine deaminase are administered to the lung. Other drugs which have been used with limited success due to difficulties in administration include vaccines, especially for flu and other respiratory illnesses, where the immune cells of the lung are the target.

Advantages of the lungs for delivery of agents having systemic effects include the large amount of surface area and ease of uptake by the mucosal surface.

It is very difficult to deliver drugs into the lungs. Even systemic delivery has limitations, since this requires administration of high dosages in order to achieve an effective concentration within the lungs.

Most drugs now are administered using a dry powder or aerosol inhaler. These devices are limited in efficacy, however, due to problems in trying to get the drugs past all of the natural barriers, such as the cilia lining the trachea, and in trying to administer a uniform volume and weight of powder.

It is therefore an object of the present invention to provide an improved composition for administration of drugs to the pulmonary system.

It is a further object of the present invention to provide a composition for controlled pulsed or sustained administration of the drugs to the pulmonary system.

SUMMARY OF THE INVENTION

Drug delivery to the pulmonary system has been achieved by encapsulation of the drug to be delivered in microparticles having a size range between 0.5 and ten microns, preferably in the range of one to five microns, formed of a material releasing drug at a pH of greater than 6.0, preferably between 6.4 and 8.0. In a preferred embodiment, the drug delivery system is based on the formation of diketopiperazine microparticles which are stable at a pH of 6.4 or less and unstable at pH of greater than 6.4, or which are stable at both acidic and basic pH, but which are unstable at pH between about 6.4 and 8. Other types of materials can also be used, including biodegradable natural and synthetic polymers, such as proteins, polymers of mixed amino acids (proteinoids), alginate, and poly(hydroxy acids). In another embodiment, the microparticles have been modified to effect targeting to specific cell types and to effect release only after reaching the targeted cells.

In the most preferred method of manufacture, the microparticles are formed in the presence of the drug to be delivered, for example, proteins or peptides such as insulin or calcitonin, polysaccharides such as heparin, nucleic acid molecules, and synthetic organic pharmaceutical compounds such as felbamate. The diketopiperazine microparticles are preferably formed in the presence of the drug to be encapsulated by: (i) acidification of weakly alkaline solutions of a diketopiperazine derivative that contains one or more acidic groups, (ii) basification of acidic solutions of a diketopiperazine derivative that contains one or more basic groups, or (iii) neutralization of an acidic or basic solution of a zwitterionic diketopiperazine derivative that contains both acidic and basic groups. The size of the resulting microparticles can be controlled by modifying the side-chains on the diketopiperazine, the concentration of various reactants, the conditions used for formation, and the process used in formation. The diketopiperazines can be symmetrically functionalized, wherein the two side-chains are identical, or they can be unsymmetrically functionalized. Both the symmetrically and unsymmetrically functionalized diketopiperazines can have side-chains that contain acidic groups, basic groups, or combinations thereof. Methods that can be used with materials other than the diketopiperazines include spray drying, phase separation, solvent evaporation, and milling, although the latter does not typically yield uniform diameters and can lead to erratic release profiles, which are not desirable. In the preferred embodiment, the microparticles are administered by the use of a dry powder—breath activated—compressed air inhaler.

Examples demonstrate the administration of calcitonin encapsulated in two micron diameter diketopiperazine microparticles to the pulmonary system of sheep.

BRIEF DESCRIPTION OF THE DRAWINGS

FIG. 1 is a prospective view of a dry powder—breath activated—compressed air, manually operated inhaler.

FIGS. 2*a* and 2*b* are graphs of the pharmacokinetics of salmon calcitonin (sCT) (100 micrograms/kg) administered to sheep by instillation into the lung (open circles) compared with administration by subcutaneous injection (closed circles), measured as plasma sCT concentration (pg/mL) over time (hours), with FIG. 1*b* representing the same data as a semi-logarithmic plot.

DETAILED DESCRIPTION OF THE INVENTION

I. Systems for Pulmonary Administration.

Microparticles having a diameter of between 0.5 and ten microns can penetrate the lungs, passing through most of the natural barriers. A diameter of less than ten microns is required to bypass the throat; a diameter of 0.5 microns or greater is required to avoid being exhaled.

A. Polymers for forming Microparticles.

A number of polymers can be used to form the microparticles. As used herein, the term "microparticles" includes microspheres (uniform spheres), microcapsules (having a core and an outer layer of polymer), and particles of irregular shape.

Polymers are preferably biodegradable within the time period over which release is desired or relatively soon thereafter, generally in the range of one year, more typically a few months, even more typically a few days to a few weeks. Biodegradation can refer to either a breakup of the microparticle, that is, dissociation of the polymers forming the microparticles and/or of the polymers themselves. This can occur as a result of change in pH from the carrier in which the particles are administered to the pH at the site of release, as in the case of the diketopiperazines, hydrolysis, as in the case of poly(hydroxy acids), by diffusion of an ion such as calcium out of the microparticle, as in the case of microparticles formed by ionic bonding of a polymer such as alginate, and by enzymatic action, as in the case of many of the polysaccharides and proteins. In some cases linear release may be most useful, although in others a pulse release or "bulk release" may provided more effective results.

Representative synthetic materials are: diketopiperazines, poly(hydroxy acids) such as poly(lactic acid), poly(glycolic acid) and copolymers thereof, polyanhydrides, polyesters such as polyorthoesters, polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), poly(octadecyl acrylate), polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications routinely made by those skilled in the art.

Bioadhesive polymers include bioerodible hydrogels described by H. S. Sawhney, C. P. Pathak and J. A. Hubell in *Macromolecules,* 1993, 26, 581–587, polyhyaluronic acids, casein, gelatin, glutin, polyanhydrides, polyacrylic acid, alginate, chitosan, and polyacrylates.

A system based upon diketopiperazine structural elements or one of its substitution derivatives, including diketomorpholines, diketodioxanes or others, forms microparticles with desirable size distributions and pH ranges as well as good cargo tolerance. A wide range of stable, reproducible characteristics can be generated with appropriate manipulations of the attachment sites, resulting in substantial yields and excellent reproducibility.

The diketopiperazines or their substitution analogs are rigid planar rings with at least six ring atoms containing heteroatoms and unbonded electron pairs. One or both of the nitrogens can be replaced with oxygen to create the substitution analogs diketomorpholine and diketodioxane, respectively. Although it is possible to replace a nitrogen with a sulfur atom, this does not yield a stable structure. The general formula for diketopiperazine and its analogs is shown below.

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O) O, —OP(O)$_2$, —P(O)$_2$O, —OS(O)$_2$, or —S(O)$_3$; U is an acid group, such as a carboxylic acid, phosphoric acid, phosphonic acid and sulfonic acid, or a basic group, such as primary, secondary and tertiary amines, quaternary ammonium salts, guanidine, aniline, heterocyclic derivatives, such as pyridine and morpholine, or a zwitterionic $C_{1-20}$ chain containing at least one acidic group and at least one basic group, for example, those described above, wherein the side chains can be further functionalized with an alkene or alkyne group at any position, one or more of the carbons on the side chain can be replaced with an oxygen, for example, to provide short polyethylene glycol chains, one or more of the carbons can be functionalized with an acidic or basic group, as described above, and wherein the ring atoms X at positions 1 and 4 are either O or N.

As used herein, "side chains" are defined as Q-T-Q-U or Q-U, wherein Q, T, and U are defined above.

Examples of acidic side chains include, but are not limited to, cis and trans —CH═CH—CO$_2$H, —CH(CH$_3$)═CH (CH$_3$)—CO$_2$H, —(CH$_2$)$_3$—CO$_2$H, —CH$_2$CH(CH$_3$)—CO$_2$H, —CH(CH$_2$CO$_2$H)═CH$_2$, -(tetrafluoro)benzoic acid, -benzoic acid and —CH(NHC(O)CF$_3$)—CH$_2$—CO$_2$H.

Examples of basic side chains include, but are not limited to, -aniline, -phenyl-C(NH)NH$_2$, -phenyl-C(NH)NH(alkyl), -phenyl-C(NH)N(alkyl)$_2$ and -(CH$_2$)$_4$NHC(O)CH(NH$_2$)CH (NH$_2$)CO$_2$H.

Examples of zwitterionic side chains include, but are not limited to, —CH(NH$_2$)—CH$_2$—CO$_2$H and —NH(CH$_2$)$_{1-20}$ CO$_2$H.

The term aralkyl refers to an aryl group with an alkyl substituent.

The term heterocyclic-alkyl refers to a heterocyclic group with an alkyl substituent.

The term alkaryl refers to an alkyl group that has an aryl substituent.

The term alkyl-heterocyclic refers to an alkyl group that has a heterocyclic substituent.

The term alkene, as referred to herein, and unless otherwise specified, refers to an alkene group of $C_2$ to $C_{10}$, and specifically includes vinyl and allyl.

The term alkyne, as referred to herein, and unless otherwise specified, refers to an alkyne group of $C_2$ to $C_{10}$.

As used herein, "diketopiperazines" includes diketopiperazines and derivatives and modifications thereof falling within the scope of the above-general formula.

The fumaryl diketopiperazine is most preferred for pulmonary applications.

B. Methods for Manufacture

The matrices can be formed of the polymers other than the diketopiperazines by solvent evaporation, spray drying, solvent extraction and other methods known to those skilled in the art. Methods developed for making microspheres for drug delivery are described in the literature, for example, as described by Mathiowitz and Langer, *J. Controlled Release* 5,13–22 (1987); Mathiowitz, et al., *Reactive Polymers* 6, 275–283 (1987); and Mathiowitz, et al., *J. Appl. Polymer Sci.* 35, 755–774 (1988), the teachings of which are incorporated herein. The selection of the method depends on the polymer selection, the size, external morphology, and crystallinity that is desired, as described, for example, by Mathiowitz, et al., *Scanning Microscopy* 4,329–340 (1990); Mathiowitz, et al., *J. Appl. Polymer Sci.* 45, 125–134 (1992); and Benita, et al., *J. Pharm. Sci.* 73, 1721–1724 (1984), the teachings of which are incorporated herein.

In solvent evaporation, described for example, in Mathiowitz, et al., (1990), Benita, and U.S. Pat. No. 4,272,398 to Jaffe, the polymer is dissolved in a volatile organic solvent. The drug, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.05 and 0.20 g/ml. After loading the solution with drug, the solution is suspended in 200 ml of vigorously stirring distilled water containing 1% (w/v) poly(vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (1–1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of DNA, preferably sieved to less than 50 $\mu$m. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used.

In spray drying, the polymer is dissolved in an organic solvent such as methylene chloride (0.04 g/ml). A known amount of active drug is suspended (if insoluble) or co-dissolved (if soluble) in the polymer solution. The solution or the dispersion is then spray-dried. Typical process parameters for a mini-spray drier are as follows: polymer concentration=0.04 g/ml, inlet temperature=24° C., outlet temperature=13 to 15° C., aspirator setting =15, pump setting =10 ml/min, spray flow =600 NLh$^{-1}$, and nozzle diameter =0.5 mm. Microspheres ranging in diameter between one and ten microns can be obtained with a morphology which depends on the selection of polymer.

Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., *Pharmazeutische Industrie* 40–111A, 1230 (1978), the teachings of which are incorporated herein. The advantage of this system is the ability to further modify the surface of the microspheres by coating them with polycationic polymers such as polylysine, after fabrication, for example, as described by Lim, et al., *J. Pharm. Sci.* 70, 351–354 (1981). For example, in the case of alginate, a hydrogel can be formed by ionically crosslinking the alginate with calcium ions, then crosslinking the outer surface of the microparticle with a polycation such as polylysine, after fabrication. The microsphere particle size will be controlled using various size extruders, polymer flow rates and gas flow rates.

Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules.

Methods for Synthesis of the Diketopiperazines

Diketopiperazines can be formed by cyclodimerization of amino acid ester derivatives, as described by Katchalski, et al., *J. Amer. Chem. Soc.* 68, 879–880 (1946), by cyclization of dipeptide ester derivatives, or by thermal dehydration of amino acid derivatives in high-boiling solvents, as described by Kopple, et al., *J. Org. Chem.* 33(2), 862–864 (1968), the teachings of which are incorporated herein. 2,5-diketo-3,6-di(aminobutyl)piperazine (Katchalski et al. refer to this as lysine anhydride) was prepared via cyclodimerization of N-epsilon-P-L-lysine in molten phenol, similar to the Kopple method in *J. Org. Chem.*, followed by removal of the blocking (P)-groups with 4.3 M HBr in acetic acid. This route is preferred because it uses a commercially available starting material, it involves reaction conditions that are reported to preserve stereochemistry of the starting materials in the product and all steps can be easily scaled up for manufacture.

Diketomorpholine and diketooxetane derivatives can be prepared by stepwise cyclization in a manner similar to that disclosed in Katchalski, et al., *J. Amer. Chem. Soc.* 68, 879–880 (1946).

Diketopiperazines can be radiolabelled. Means for attaching radiolabels are known to those skilled in the art. Radiolabelled diketopiperazines can be prepared, for example, by reacting tritium gas with those compounds listed above that contain a double or triple bond. A carbon-14 radiolabelled carbon can be incorporated into the side chain by using $^{14}C$ labelled precursors which are readily available. These radio-labelled diketopiperazines can be detected in vivo after the resulting microparticles are administered to a subject.

Synthesis of Symmetrical Diketopiperazine Derivatives

The diketopiperazine derivatives are symmetrical when both side chains are identical. The side chains can contain acidic groups, basic groups, or combinations thereof.

One example of a symmetrical diketopiperazine derivative is 2,5-diketo-3,6-di(4-succinylaminobutyl)piperazine. 2,5-diketo-3,6-di(aminobutyl)piperazine is exhaustively succinylated with succinic anhydride in mildly alkaline aqueous solution to yield a product which is readily soluble in weakly alkaline aqueous solution, but which is quite insoluble in acidic aqueous solutions. When concentrated solutions of the compound in weakly alkaline media are rapidly acidified under appropriate conditions, the material separates from the solution as microparticles.

Other preferred compounds can be obtained by replacing the succinyl group(s) in the above compound with glutaryl, maleyl or fumaryl groups.

Unsymmetrical Diketopiperazine Derivatives Unsymmetric deprotection of a symmetrical diketopiperazine intermediate.

One method for preparing unsymmetrical diketopiperazine derivatives is to protect functional groups on the side chain, selectively deprotect one of the side chains, react the deprotected functional group to form a first side chain, deprotect the second functional group, and react the deprotected functional group to form a second side chain.

Diketopiperazine derivatives with protected acidic side chains, such as cyclo-Lys(P)Lys(P), wherein P is a benzyloxycarbonyl group, or other protecting group known to those skilled in the art, can be selectively deprotected. The protecting groups can be selectively cleaved by using limiting reagents, such as HBr in the case of the benzyloxycarbonyl group, or fluoride ion in the case of silicon protecting groups, and by using controlled time intervals. In this manner, reaction mixtures which contain unprotected, monoprotected and di-protected diketopiperazine derivatives can be obtained. These compounds have different solubilities in various solvents and pH ranges, and can be separated by selective precipitation and removal. An appropriate solvent, for example, ether, can then be added to such reaction mixtures to precipitate all of these materials together. This can stop the deprotection reaction before completion by removing the diketopiperazines from the reactants used to deprotect the protecting groups. By stirring the mixed precipitate with water, both the partially and completely reacted species can be dissolved as salts in the aqueous medium. The unreacted starting material can be removed by centrifugation or filtration. By adjusting the pH of the aqueous solution to a weakly alkaline condition, the asymmetric monoprotected product containing a single protecting group precipitates from the solution, leaving the completely deprotected material in solution.

In the case of diketopiperazine derivatives with basic side chains, the basic groups can also be selectively deprotected. As described above, the deprotection step can be stopped before completion, for example, by adding a suitable solvent to the reaction. By carefully adjusting the solution pH, the diprotected derivative can be removed by filtration, leaving the partially and totally deprotected derivatives in solution. By adjusting the pH of the solution to a slightly acidic condition, the monoprotected derivative precipitates out of solution and can be isolated.

Zwitterionic diketopiperazine derivatives can also be selectively deprotected, as described above. In the last step, adjusting the pH to a slightly acidic condition precipitates the monoprotected compound with a free acidic group. Adjusting the pH to a slightly basic condition precipitates the monoprotected compound with a free basic group.

Limited removal of protecting groups by other mechanisms, including but not limited to cleaving protecting groups that are cleaved by hydrogenation by using a limited amount of hydrogen gas in the presence of palladium catalysts. The resulting product is also an asymmetric partially deprotected diketopiperazine derivative. These derivatives can be isolated essentially as described above.

The monoprotected diketopiperazine is reacted to produce a diketopiperazine with one sidechain and protecting group. Removal of protecting groups and coupling with other side chains yields unsymmetrically substituted diketopiperazines with a mix of acidic, basic, and zwitterionic sidechains.

Other materials that exhibit this response to pH can be obtained by functionalizing the amide ring nitrogens of the diketopiperazine ring.

Methods for forming microparticles and encapsulating drug

In one embodiment, drug is encapsulated within microparticles by dissolving a diketopiperazine with acidic side chains in bicarbonate or other basic solution, adding the drug in solution or suspension to be encapsulated, then precipitating the microparticle by adding acid, such as 1 M citric acid.

In a second embodiment, drug is encapsulated within microparticles by dissolving a diketopiperazine with basic side chains in an acidic solution, such as 1 M citric acid, adding the drug in solution or suspension to be encapsulated, then precipitating the microparticle by adding bicarbonate or other basic solution.

In a third embodiment, drug is encapsulated within microparticles by dissolving a diketopiperazine with both acidic and basic side chains in an acidic or basic solution, adding the drug in solution or suspension to be encapsulated, then precipitating the microparticle by neutralizing the solution.

The microparticles can be stored in the dried state and suspended for administration to a patient. In the first embodiment, the reconstituted microparticles maintain their stability in an acidic medium and dissociate as the medium approaches physiological pH in the range of between 6 and 14. In the second embodiment, suspended microparticles maintain their stability in a basic medium and dissociate at a pH of between 0 and 6. In the third embodiment, the reconstituted microparticles maintain their stability in an acidic or basic medium and dissociate as the medium approaches physiological pH in the range of pH between 6 and 8.

II. Selection and Incorporation of Drugs.

A. Drugs to be incorporated.

Generally speaking, any form of drug can be delivered. Examples include synthetic inorganic and organic compounds, proteins and peptides, polysaccharides and other sugars, lipids, and nucleic acid sequences having therapeutic, prophylactic or diagnostic activities. The agents to be incorporated can have a variety of biological activities, such as vasoactive agents, neuroactive agents, hormones, anticoagulants, immunomodulating agents, cytotoxic agents, antibiotics, antivirals, antisense, antigens, and antibodies. In some instances, the proteins may be antibodies or antigens which otherwise would have to be administered by injection to elicit an appropriate response. More particularly, compounds that can be encapsulated include insulin, heparin, calcitonin, felbamate, parathyroid hormone and fragments thereof, growth hormone, erythropoietin, AZT, DDI, G-CSF, lamotrigine, chorionic gonadotropin releasing factor, luteinizing releasing hormone, β-galactosidase and Argatroban. Compounds with a wide range of molecular weight can be encapsulated, for example, between 100 and 500,000 grams per mole.

Natural Biological Molecules Proteins are defined as consisting of 100 amino acid residues or more; peptide are less than 100 amino acid residues. Unless otherwise stated, the term protein refers to both proteins and peptides. Examples include insulin and other hormones. Polysaccharides, such as heparin, can also be administered.

The drug can be administered as an antigen, where the molecule is intended to elicit a protective immune response, especially against an agent that preferentially infects the lungs, such as mycoplasma, bacteria causing pneumonia, and respiratory synticial virus. In these cases, it may also be useful to administer the drug in combination with an adjuvant, to increase the immune response to the antigen.

Nucleic Acid Sequences

Any genes that would be useful in replacing or supplementing a desired function, or achieving a desired effect such as the inhibition of tumor growth, could be introduced using the matrices described herein. As used herein, a "gene" is an isolated nucleic acid molecule of greater than thirty nucleotides, preferably one hundred nucleotides or more, in length. Examples of genes which replace or supplement function include the genes encoding missing enzymes such as adenosine deaminase (ADA) which has been used in clinical trials to treat ADA deficiency and cofactors such as insulin and coagulation factor VIII. Genes which effect regulation can also be administered, alone or in combination with a gene supplementing or replacing a specific function. For example, a gene encoding a protein which suppresses expression of a particular protein-encoding gene, or vice versa, which induces expresses of a protein-encoding gene, can be administered in the matrix. Examples of genes which are useful in stimulation of the immune response include viral antigens and tumor antigens, as well as cytokines (tumor necrosis factor) and inducers of cytokines (endotoxin), and various pharmacological agents.

Other nucleic acid sequences that can be utilized include antisense molecules which bind to complementary DNA to inhibit transcription, ribozyme molecules, and external guide sequences used to target cleavage by RNAase P, as described by S. Altman, et al., of Yale University.

As used herein, vectors are agents that transport the gene into targeted cells and include a promoter yielding expression of the gene in the cells into which it is delivered. Promoters can be general promoters, yielding expression in a variety of mammalian cells, or cell specific, or even nuclear versus cytoplasmic specific. These are known to those skilled in the art and can be constructed using standard molecular biology protocols. Vectors increasing penetration, such as lipids, liposomes, lipid conjugate forming molecules, surfactants, and other membrane permeability enhancing agents are commercially available and can be delivered with the nucleic acid.

Imaging Agents

Imaging agents including metals, radioactive isotopes, radioopaque agents, fluorescent dyes, and radiolucent agents can also be incorporated. Radioisotopes and radioopaque agents include gallium, technetium, indium, strontium, iodine, barium, and phosphorus.

B. Loading of Drug.

The range of loading of the drug to be delivered is typically between about 0.01% and 90%, depending on the form and size of the drug to be delivered and the target tissue. In the preferred embodiment using diketopiperazines, the preferred range is from 0.1% to 50% loading by weight of drug.

C. Pharmaceutical Compositions.

The microparticles can be suspended in any appropriate pharmaceutical carrier, such as saline, for administration to a patient. In the most preferred embodiment, the microparticles will be stored in dry or lyophilized form until immediately before administration. They can then be suspended in sufficient solution, for example an aqueous solution for administration as an aerosol, or administered as a dry powder.

D. Targeted Administration.

The microparticles can be delivered to specific cells, especially phagocytic cells and organs. Phagocytic cells within the Peyer's patches appear to selectively take up microparticles administered orally. Phagocytic cells of the reticuloendothelial system also take up microparticles when administered intravenously. Endocytosis of the microparticles by macrophages in the lungs can be used to target the microparticles to the spleen, bone marrow, liver and lymph nodes.

The microparticles can also be targeted by attachment of ligands which specifically or non-specifically bind to particular targets. Examples of such ligands include antibodies and fragments including the variable regions, lectins, and hormones or other organic molecules having receptors on the surfaces of the target cells.

The charge or lipophilicity of the microparticle is used to change the properties of the protein carrier. For example, the lipophilicity can be modified by linking lipophilic groups to increase affinity of some drugs for the microencapsulation system, thereby increasing drug cargo capacity. Other modifications can be made before or after formation of the microparticle, as long as the modification after formation does not have a detrimental effect on the incorporated compound.

E. Storage of the Microparticles.

In the preferred embodiment, the microparticles are stored lyophilized. The dosage is determined by the amount of encapsulated drug, the rate of release within the pulmonary system, and the pharmacokinetics of the compound.

III. Delivery of Microparticles.

The microparticles can be delivered using a variety of methods, ranging from administration directly into the nasal passages so that some of the particles reach the pulmonary system, to the use of a powder instillation device, to the use of a catheter or tube reaching into the pulmonary tract. Dry powder inhalers are commercially available, although those using hydrocarbon propellants are no longer used and those relying on the intake of a breath by a patient can result in a variable dose.

FIG. 1 is a schematic of a preferred dry powder—breath activated—compressed air, manually operated inhaler 10. A gel cap 12, or other container which is easily ruptured, filled with the proper dose and volume of microparticulates containing drug to be delivered, or the microparticulates per se, 14 is inserted into the top 16 of the chamber to make an air seal. Manual activation of the plunger 18 by the patient ruptures the gel cap 12, allowing its contents to fall into the reservoir 20. When the patient inhales, this causes the hinged, breath activated valve 22 to open, releasing the pressurized air into the powder reservoir 20, dispersing the powder 24 into the air stream at the optimum moment in the inhalation cycle. The air pump 26 is manually operated by the patient to fill the air reservoir 28 to a predetermined pressure. Further pumping by the patient produces an audible whistle through the relief valve 30, indicating that the inhaler 10 is ready for use.

In a variation of this device, the gel cap 12 and plunger 18 is replaced with a sealable opening which allows for insertion of a metered amount of powder or microparticulates into the reservoir.

The present invention will be further understood by reference to the following non-limiting examples.

EXAMPLE 1

Administration of calcitonin-diketopiperazine microparticles to sheep.

Materials and Methods

Animals

Sheep (approximately 100 kg) were housed at SUNY Stony Brook Health Sciences Center. Animals were anesthetized with acepromazine/thiopental sodium. A suspense of diketopiperazine microparticle/sCT (10.04 mg/mL in 0.9% saline) was instilled in each lung of each sheep. A solution of sCT (10 mg/mL in 0.9% saline) was administered by subcutaneous injection to control animals. An intravenous catheter was placed in the cephalic vein of each anesthetized animal for blood sampling.

Dosing Solutions and Calculations The following dosing solutions were prepared on the day of the experiment. The volume of the dose delivered was calculated based on the actual weight of the animal as described below.

Suspension: Microparticle/sCT [2.47%sCT by weight] 10.04 mg/mL in 0.9% saline (pH 5.5)

Solution: 10 mg/mL sCT in 0.9% saline (pH 5.5)

Calculation: Actual volume per sheep =(Wt subject/100 kg)×Vol/sheep

Blood Sampling and Processing

Blood samples were drawn at the following time points: −5, 0 (predose), 1, 3, 5, 10, 15, 30, 45, 60, 90 minutes, 2, 4, and 6 hours. Blood samples (3 mL) were collected by the intravenous line which was washed with 0.9% saline containing heparin following each sample. Samples were collected in heparinized vacutainer tubes (Becton Dickinson #6387 Vacutainer Tubes (45 units USP sodium heparin), 3 mL draw, 64×10.25 mm] and placed on ice until processing. Tubes were centrifuged at 2000 rpm for 15 minutes and plasma harvested immediately. Plasma was frozen on dry ice and stored at −400° C. until analysis.

Sample Analysis

Plasma sCT concentration was determined using radioimmunoassay (Research and Diagnostic Antibodies, Berkeley, Calif., catalog #K-1235).

Study Design

The pharmacokinetics of sCT in sheep was determined after lung instillation of a formulation of sCT in diketopiperazine microparticle (2.47% by weight sCT) at a sCT dose of 100 µg/kg. The results were compared with 100 µg/kg sCT administered by subcutaneous injection as a solution in 0.9% saline. This study consisted of a crossover experiment in which each sheep was administered a suspension of diketopiperazine microparticles/sCT by instillation in the lung. One week later each sheep received a subcutaneous injection of sCT in 0.9% saline at the same dose.

Results

The mean pharmacokinetic profiles of plasma sCT delivered to the lung and subcutaneously were determined by radioimmunoassay. The absorption in both the pulmonary and subcutaneous administrations was rapid with significant blood levels appearing within 30 minutes.

The truncated AUC (0 to 6 hours) was calculated for each animal using the trapezoidal rule. The bioavailability (F%) for each animal was calculated from the ration of the AUCs for the pulmonary and subcutaneous administrations. The mean (±standard error of the mean) AUC for the pulmonary and subcutaneous administration was 6,505±1,443 pg.hr/mL and 38,842±5,743 pg.hr/mL, respectively. The mean (+standard error of the mean) of the individual animal bioavailabilities was 17±4%.

The mean (±standard error of the mean) peak plasma sCT level following pulmonary administration was 2,864±856 pg/mL and occurred at 0.25 hours. The mean peak level following subcutaneous administration was 9,407±1,792 pg/mL and occurred at 2 hours. The peak sCT level for the pulmonary administration was 32% of that for the subcutaneous administration.

Figure 1:
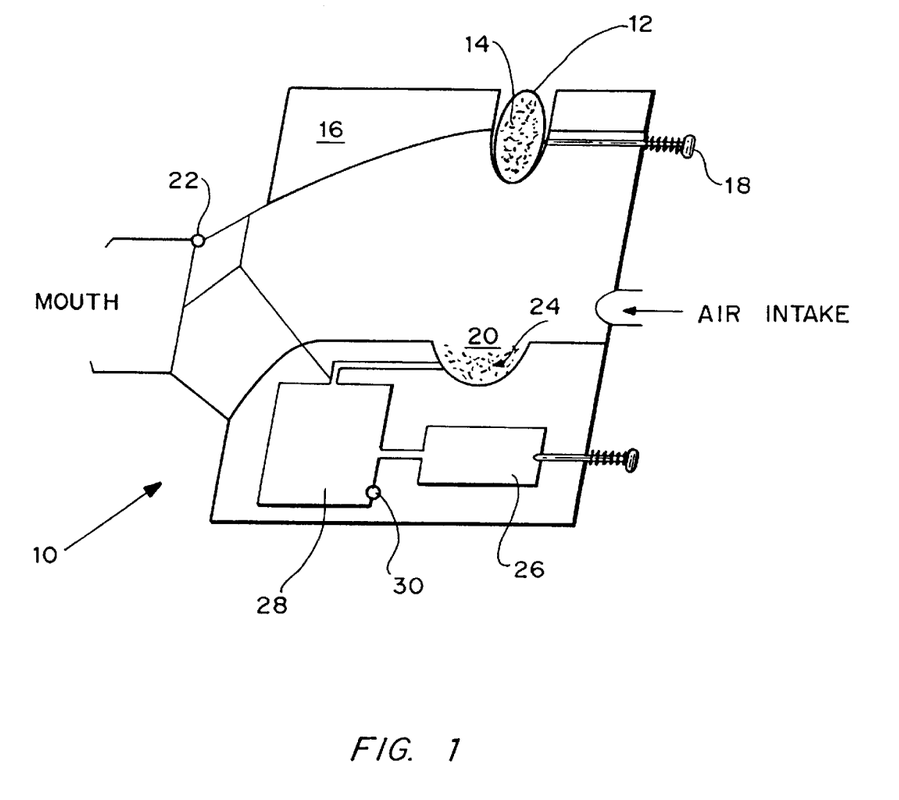
Figure 2A:
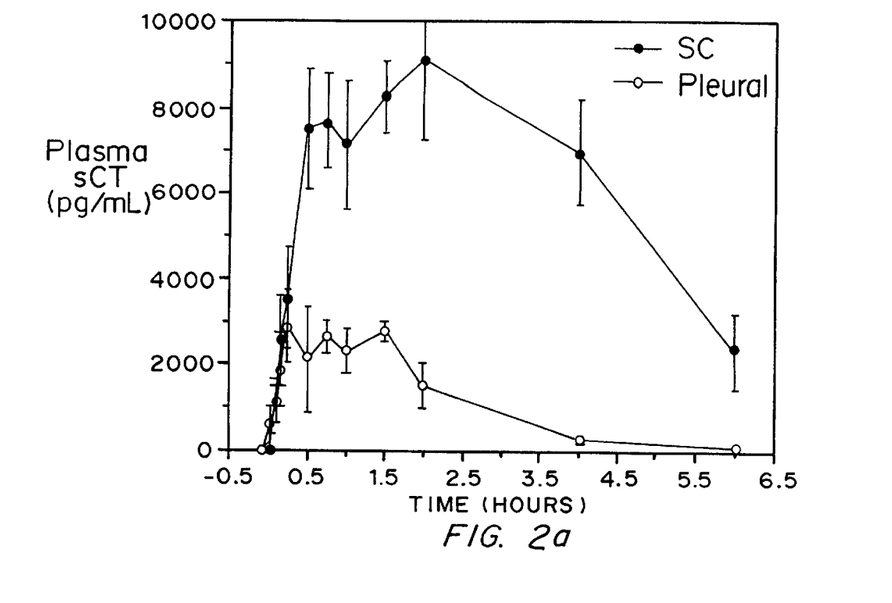
Figure 2B:
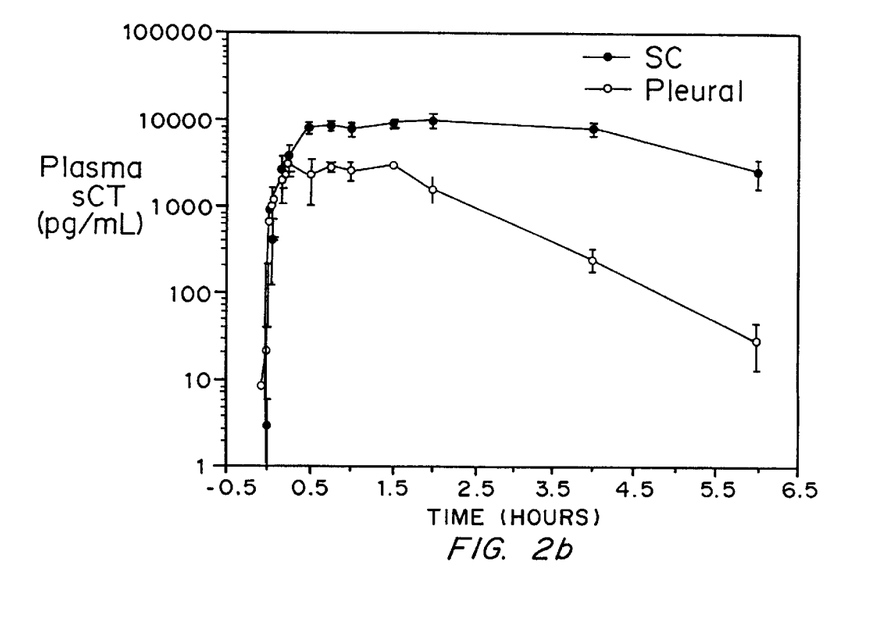

These results are shown in FIGS. 2a and 2b.

Discussion

These results show that sCT is absorbed into the blood stream when administered to the lung of sheep using the diketopiperazine microparticle formulation. The plot of the mean plasma sCT levels for the pulmonary and subcutaneous administrations of sCT shows that the subject to subject variability in the routes of delivery is comparable. The bioavailability of the pulmonary route in this preliminary analysis was 17% versus the subcutaneous administration.

These data clearly show that sCT is absorbed when administered to the lung in a diketopiperazine microparticle formulation.

Modifications and variations of the compositions and methods of the present invention will be obvious to those skilled in the art from the foregoing detailed description. Such modifications and variations are intended to come within the scope of the appended claims.

We claim:

1. A microparticulate system for drug delivery to the pulmonary system comprising:

synthetic biodegradable microparticles which comprise a diketopiperazine and which have a diameter between 0.5 microns and ten microns and which release an incorporated therapeutic, prophylactic, or diagnostic agent at a pH of 6.0 or greater, in a pharmaceutically acceptable carrier for administration to the lungs.

2. The system of claim 1 wherein the microparticles further comprise a material selected from the group consisting of poly(hydroxy acids), polyanhydrides, polyesters, polyamides, polycarbonates, polyalkylenes, polyvinyl compounds, polysiloxanes, polymers of acrylic and methacrylic acids, polyurethanes and co-polymers thereof, celluloses, poly(butic acid), poly(valeric acid), poly(lactide-co-caprolactone), polysaccharides, proteins, copolymers and mixtures thereof.

3. The system of claim 2 wherein the material is a polyhydroxy acid.

4. The system of claim 1 wherein the therapeutic, prophylactic or diagnostic agent is selected from the group consisting of proteins, polysaccharides, lipids, nucleic acids, other synthetic organic pharmaceutical compounds, and combinations thereof.

5. The system of claim 4 wherein the agent is selected from the group consisting of insulin, calcitonin, felbamate, heparin, parathyroid hormone and fragments thereof, growth hormone, erythropoietin, AZT, DDI, G CSF, lamotrigine, chorionic gonadotropin releasing factor, luteinizing releasing hormone, vaccines, gene encoding adenosine deaminase, and Argatroban.

6. The system of claim 1 wherein the microparticles are a dry powder provided with an apparatus for administration of the microparticles to the lungs.

7. A method for delivery of particles to the pulmonary system comprising:

administering to a patient in need of treatment an effective amount of synthetic biodegradable microparticles which comprise a diketopiperazine and which have a diameter between 0.5 microns and ten microns, in a pharmaceutically acceptable carrier for administration to the lungs.

8. The method of claim 7 wherein the microparticles further comprise a material selected from the group consisting of poly(hydroxy acids), polyanhydrides, polyesters, polyamides, polycarbonates, polyalkylenes, polyvinyl compounds, polysiloxanes, polymers of acrylic and methacrylic acids, polyurethanes and co-polymers thereof, celluloses, poly(butic acid), poly(valeric acid), poly(lactide-co-caprolactone), polysaccharides, proteins, copolymers and mixtures thereof.

9. The method of claim 8 wherein the material is a polyhydroxy acid.

10. The method of claim 7 wherein the microparticles further comprise a therapeutic, prophylactic, or diagnostic agent selected from the group consisting of proteins, polysaccharides, lipids, nucleic acids, other synthetic organic pharmaceutical compounds, and combinations thereof.

11. The method of claim 10 wherein the agent is selected from the group consisting of insulin, calcitonin, felbamate, heparin, parathyroid hormone and fragments thereof, growth hormone, erythropoietin, AZT, DDI, G CSF, lamotrigine, chorionic gonadotropin releasing factor, luteinizing releasing hormone, β-galactosidase and Argatroban.

12. The method of claim 7 wherein the microparticles are a dry powder provided with an apparatus for administration of the microparticles to the lungs.

13. The system of claim 1 wherein the therapeutic, prophylactic, or diagnostic agent is selected from the group consisting of vasoactive agents, neuroactive agents, hormones, anticoagulants, immunomodulating agents, cytotoxic agents, antibiotics, antivirals, antisense, antigens, and antibodies.

14. The method of claim 7 wherein the therapeutic, prophylactic, or diagnostic agent is selected from the group consisting of vasoactive agents, neuroactive agents, hormones, anticoagulants, immunomodulating agents, cytotoxic agents, antibiotics, antivirals, antisense, antigens, and antibodies.

* * * * *

UNITED STATES PATENT AND TRADEMARK OFFICE
CERTIFICATE OF CORRECTION

PATENT NO. : 6,071,497

DATED : June 6, 2000

INVENTOR(S) : Solmon S. Steiner, Robert Feldstein, Huiling Lian, Christopher A. Rhodes, and Gregory S. Shen It is certified that error appears in the above-identified patent and that said Letters Patent is hereby corrected as shown below:

On the Title Page:

[54] delete the title "MICROPARTICLES FOR LUNG DELIVERY COMPRISING DIKETOPIPERAZINE" and insert the title
--METHOD FOR DRUG DELIVERY TO THE PULMONARY SYSTEM--

Signed and Sealed this

Twenty-seventh Day of March, 2001

*Attest:*

NICHOLAS P. GODICI

*Attesting Officer*  Acting Director of the United States Patent and Trademark Office